US010512525B2

(12) United States Patent
Fisker

(10) Patent No.: US 10,512,525 B2
(45) Date of Patent: Dec. 24, 2019

(54) MODELING AND MANUFACTURING OF DENTURES

(71) Applicant: 3SHAPE A/S, Copenhagen K (DK)

(72) Inventor: Rune Fisker, Virum (DK)

(73) Assignee: 3SHAPE A/S, Copenhagen K (DK)

( * ) Notice: Subject to any disclaimer, the term of this patent is extended or adjusted under 35 U.S.C. 154(b) by 461 days.

(21) Appl. No.: 15/402,874

(22) Filed: Jan. 10, 2017

(65) Prior Publication Data

US 2017/0112600 A1 Apr. 27, 2017

Related U.S. Application Data

(63) Continuation of application No. 13/877,064, filed as application No. PCT/DK2011/050370 on Sep. 30, 2011, now Pat. No. 9,566,138.

(Continued)

(30) Foreign Application Priority Data

Oct. 1, 2010 (DK) .................................. 2010 00893

(51) Int. Cl.
*A61C 8/00* (2006.01)
*B33Y 80/00* (2015.01)
(Continued)

(52) U.S. Cl.
CPC .......... *A61C 8/0062* (2013.01); *A61C 8/0048* (2013.01); *A61C 8/0077* (2013.01);
(Continued)

(58) Field of Classification Search
CPC ... A61C 8/0048; A61C 8/0062; A61C 8/0077; A61C 13/01; A61C 13/102; A61C 13/2656; Y10T 29/49567
See application file for complete search history.

(56) References Cited

U.S. PATENT DOCUMENTS 5,725,376 A * 3/1998 Poirier .................. A61C 1/084
433/172
7,040,896 B2 * 5/2006 Pavlovskaia ........... A61C 7/002
433/215
(Continued)

FOREIGN PATENT DOCUMENTS

CN 1784187 A 6/2006
CN 101548911 A 10/2009
(Continued)

OTHER PUBLICATIONS

International Search Report (PCT/ISA/210) dated Dec. 19, 2011, by the Nordic Patent Institute as the International Searching Authority for International Application No. PCT/DK2011/050370.
(Continued)

*Primary Examiner* — Jennifer L Norton
(74) *Attorney, Agent, or Firm* — Buchanan Ingersoll & Rooney PC

(57) ABSTRACT

A method for creating a digital model of a denture for a patient, where the denture includes a gingival part and artificial teeth, includes obtaining digital models of artificial teeth representing the artificial teeth; obtaining a 3D scan comprising a digital representation of at least part of the patient's existing gingiva; digitally modeling a gingival part of the digital model of the denture using the 3D scan and the digital artificial teeth; digitally determining a first offset defining a first thickness of a first portion of the gingival part of the digital model of the denture that extends from the digital representation of the at least part of the patient's existing gingiva; and digitally determining a second offset defining a second thickness of a second portion of the gingival part of the digital model of the denture that extends from the digital artificial teeth.

23 Claims, 13 Drawing Sheets

Related U.S. Application Data

(60) Provisional application No. 61/388,956, filed on Oct. 1, 2010.

(51) Int. Cl.
| | | |
|---|---|---|
| *A61C 13/10* | (2006.01) | |
| *A61C 13/01* | (2006.01) | |
| *A61C 13/00* | (2006.01) | |
| *A61C 9/00* | (2006.01) | |
| *A61C 13/265* | (2006.01) | |

(52) U.S. Cl.
CPC ........ *A61C 9/0053* (2013.01); *A61C 13/0004* (2013.01); *A61C 13/01* (2013.01); *A61C 13/102* (2013.01); *B33Y 80/00* (2014.12); *A61C 13/2656* (2013.01); *Y10T 29/49567* (2015.01)

(56) References Cited

U.S. PATENT DOCUMENTS

| | | | |
|---|---|---|---|
| 7,758,345 B1 * | 7/2010 | Christensen | A61C 9/00 433/214 |
| 8,582,870 B2 * | 11/2013 | Glor | A61C 1/084 382/154 |
| 9,411,910 B2 * | 8/2016 | Methot | A61C 13/0004 |
| 9,566,138 B2 | 2/2017 | Fisker | |
| 2002/0180760 A1 * | 12/2002 | Rubbert | G16H 50/50 345/630 |
| 2003/0096210 A1 | 5/2003 | Rubbert et al. | |
| 2004/0219490 A1 | 11/2004 | Gartner | |
| 2006/0040236 A1 | 2/2006 | Schmitt | |
| 2006/0120582 A1 * | 6/2006 | Squilla | A61C 13/0004 382/128 |
| 2006/0253212 A1 | 11/2006 | Weber | |
| 2007/0009852 A1 | 1/2007 | Childress | |
| 2007/0190492 A1 | 8/2007 | Schmitt | |
| 2008/0124677 A1 | 5/2008 | Ertl | |
| 2008/0187887 A1 * | 8/2008 | Lu | A61C 13/0006 433/215 |
| 2009/0148813 A1 | 6/2009 | Sun | |
| 2009/0287332 A1 | 11/2009 | Adusumilli et al. | |
| 2009/0306939 A1 | 12/2009 | Methot | |
| 2010/0086899 A1 | 4/2010 | Holzner et al. | |
| 2010/0119996 A1 | 5/2010 | Kaigler, Sr. | |
| 2011/0196654 A1 | 8/2011 | Genest | |
| 2011/0236856 A1 | 9/2011 | Kanagawa et al. | |
| 2012/0029682 A1 | 2/2012 | Basler et al. | |
| 2012/0095732 A1 | 4/2012 | Fisker | |
| 2012/0179281 A1 | 7/2012 | Steingart | |
| 2012/0230566 A1 | 9/2012 | Dean | |
| 2012/0258430 A1 | 10/2012 | Ruppert et al. | |
| 2012/0276502 A1 * | 11/2012 | Marshall | G05B 19/4099 433/199.1 |
| 2013/0060532 A1 | 3/2013 | Clausen | |
| 2014/0051037 A1 * | 2/2014 | Fisker | A61C 8/0048 433/213 |
| 2014/0317930 A1 * | 10/2014 | Klingenburg | A61C 13/0004 29/896.1 |
| 2016/0100917 A1 | 4/2016 | Howe | |
| 2017/0112600 A1 | 4/2017 | Fisker | |
| 2019/0060036 A1 * | 2/2019 | Fisker | A61C 13/0004 |
| 2019/0247166 A1 * | 8/2019 | Kirsten | A61C 13/0006 |
| 2019/0247169 A1 * | 8/2019 | Fisker | A61C 13/1003 |

FOREIGN PATENT DOCUMENTS

| | | |
|---|---|---|
| CN | 201558185 U | 8/2010 |
| EP | 2 621 397 | 8/2013 |
| JP | 59-189839 A | 10/1984 |
| JP | 11-128248 A | 5/1999 |
| JP | 2003-135489 A | 5/2003 |
| RU | 2 384 308 C2 | 3/2010 |
| WO | WO 96/01083 A1 | 1/1996 |
| WO | WO 2010/058822 A1 | 5/2010 |
| WO | WO 2011/066895 A1 | 6/2011 |
| WO | 2012/041329 A1 | 4/2012 |

OTHER PUBLICATIONS

An English language translation of the Office Action (First Office Action) dated Nov. 20, 2014, in corresponding Chinese Patent Application No. 201180057779.5. (17 pages).

Supplementary European Search Report dated May 4, 2015, issued by the European Patent Office in the corresponding European Application No. 11828161.7. (6 pages).

The extended European Search Report dated Oct. 14, 2015, by the European Patent Office in corresponding European Patent Application No. 11828161.7-1658. (10 pages).

Office Action dated Jul. 31, 2017, by the Canadian Intellectual Property Office in Canadian Patent Application No. 2,813,054 (4 pages).

English language translation of the Office Action (First Office Action) dated Nov. 20, 2014, in corresponding Chinese Patent Application No. 201180057779.5. (17 pages).

English language translation of Office Action (Notice of Reasons for Rejection) dated Aug. 11, 2015, by the Japanese Patent Office in corresponding Japanese Patent Application No. 2013-530570. (3 pages).

English language translation of Office Action dated Oct. 1, 2015, by the Russian Patent Office in corresponding Russian Patent Application No. 2013119463/14(028881). (5 pages).

\* cited by examiner

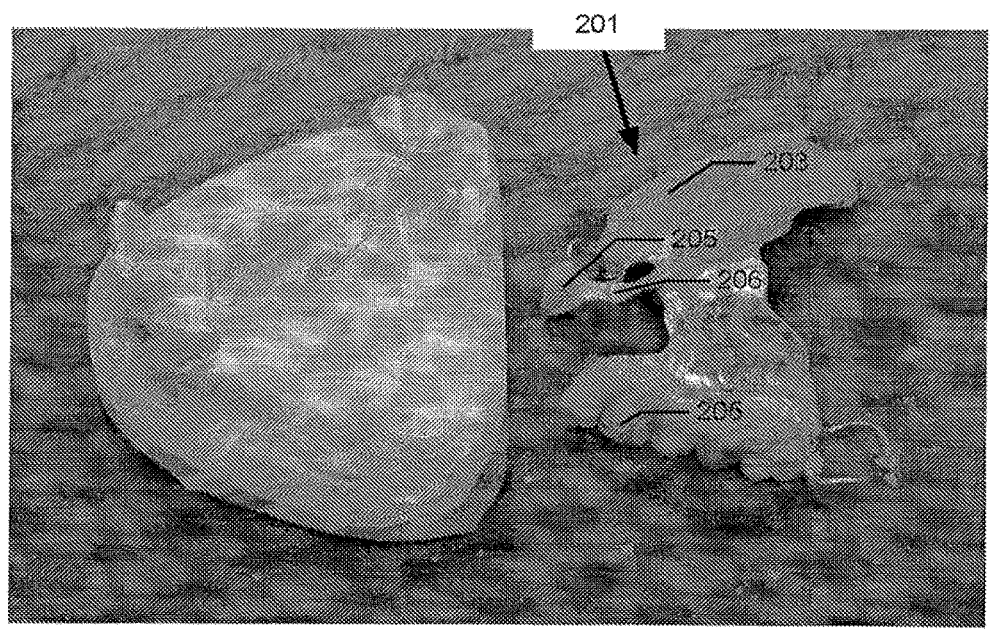
Fig. 2a)
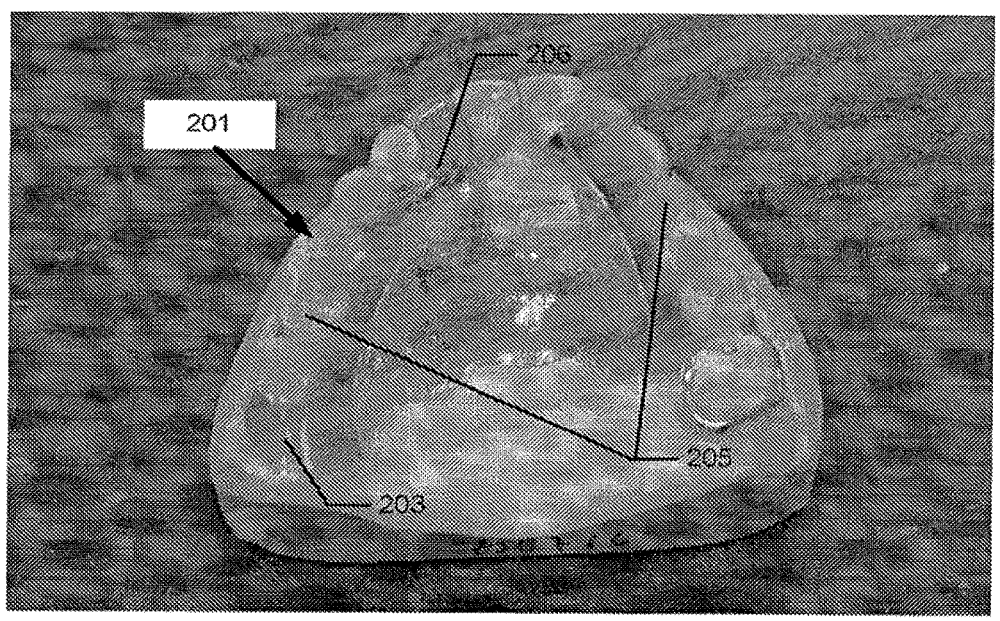

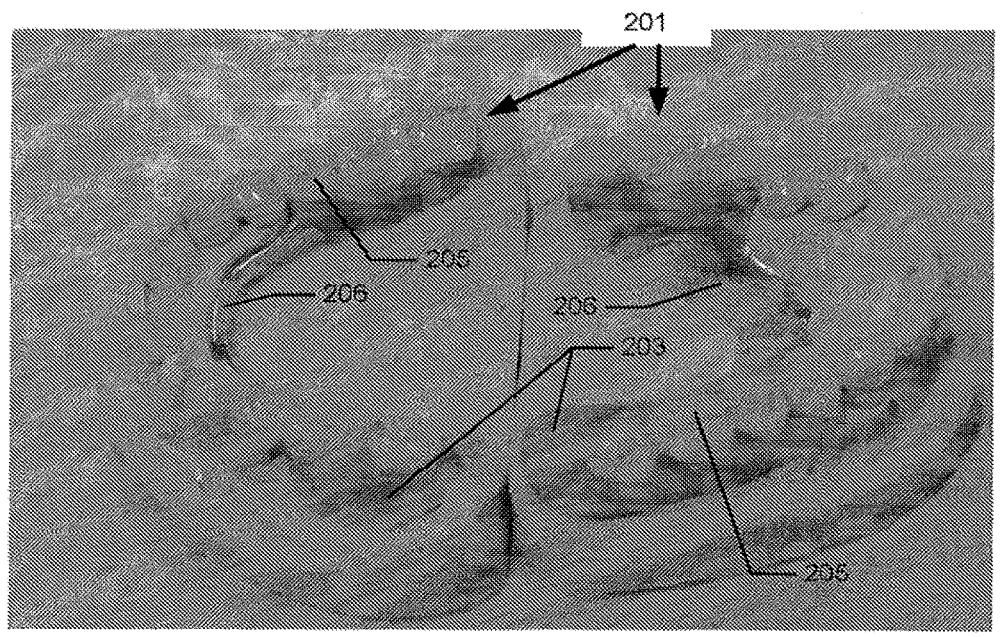
Fig. 2b)

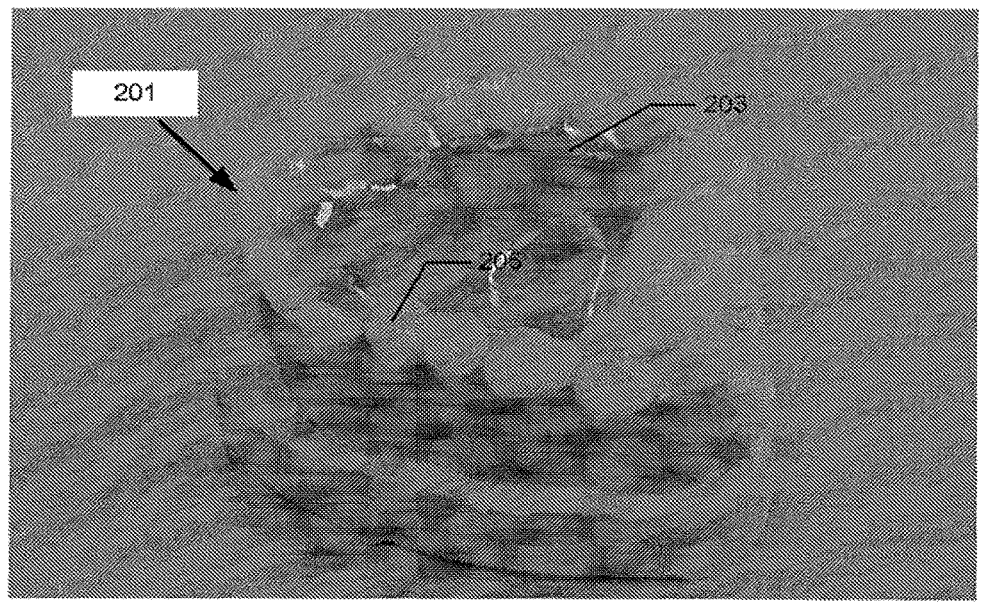
Fig. 2c)
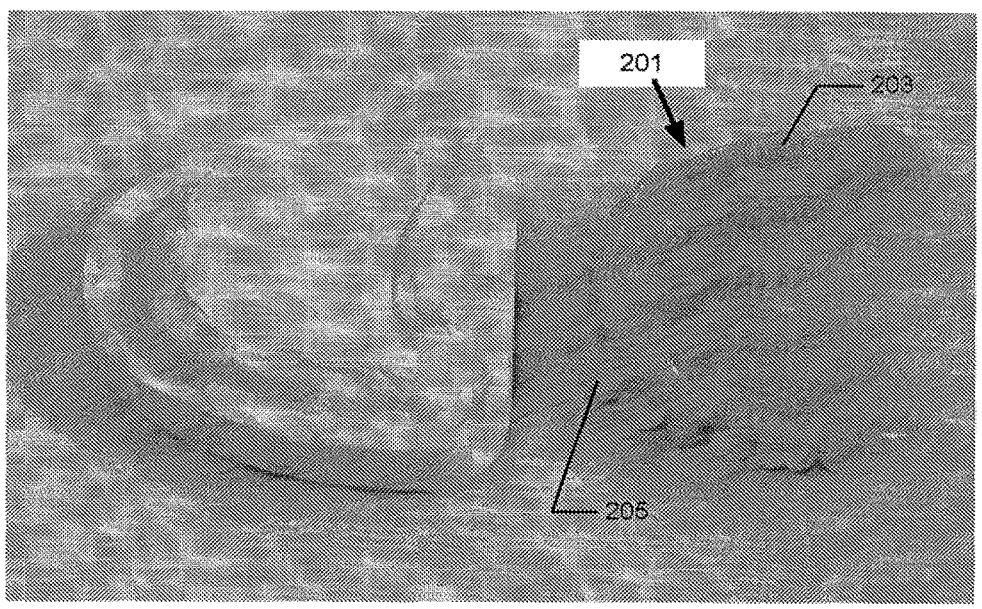

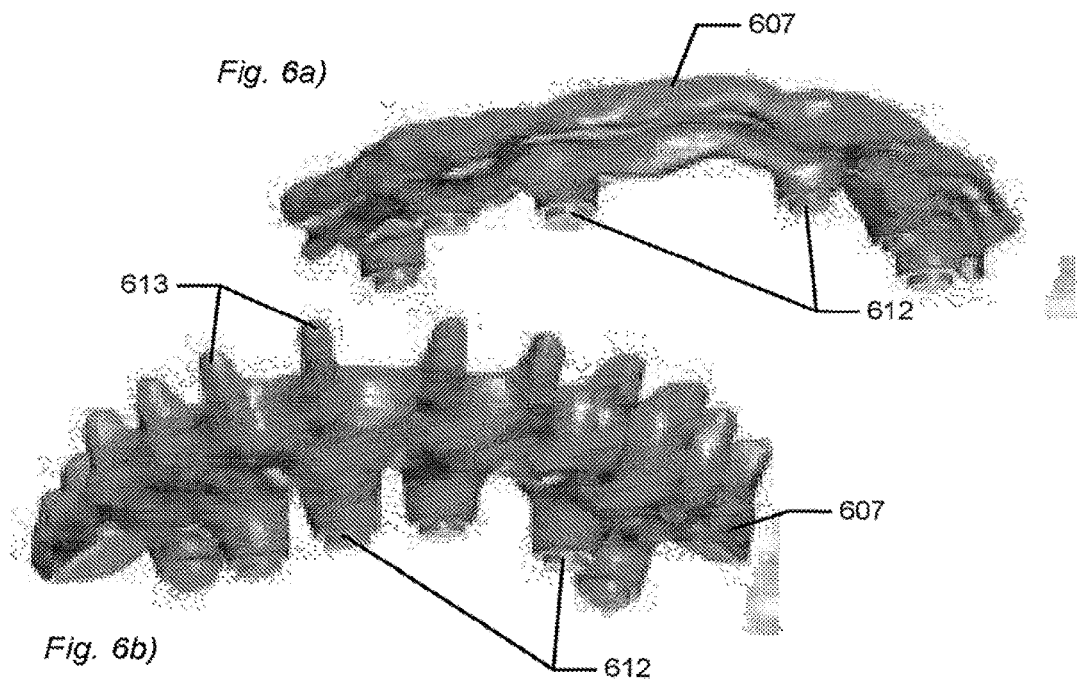
Fig. 6a)
Fig. 6b)
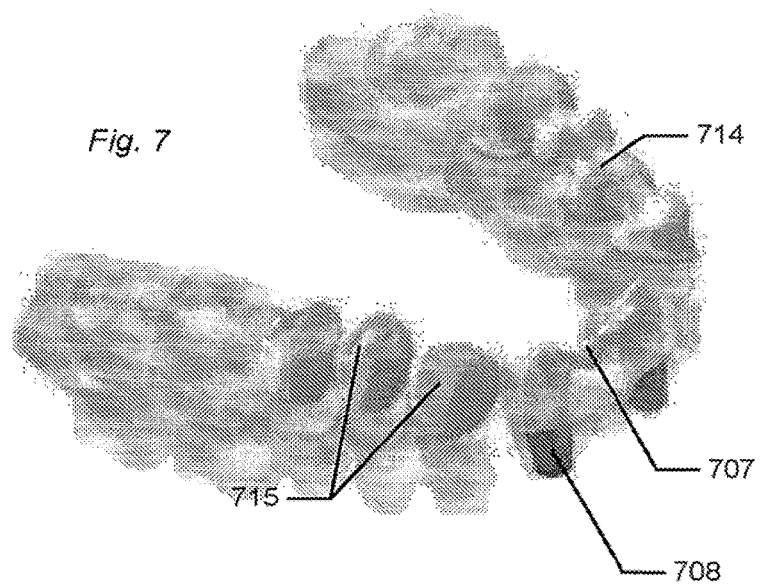
Fig. 7

MODELING AND MANUFACTURING OF DENTURES

CROSS-REFERENCE TO RELATED APPLICATIONS

The present application is a continuation of U.S. Ser. No. 13/877,064, which is a national stage application of PCT/DK11/50370, filed on Sep. 30, 2011, and which claims the priority of U.S. 61/388,956, which was filed on Oct. 1, 2010, and DK Application No. PA 2010 00893, which was filed on Oct. 1, 2010. U.S. Ser. No. 13/877,064; PCT/DK11/50370; U.S. 61/388,956; and DK Application No. PA 2010 00893 are all incorporated herein by reference.

FIELD OF THE INVENTION

This invention generally relates to a method for modeling and manufacturing a denture for a patient. In particular the invention relates to computer-implemented modeling.

BACKGROUND

US2009287332 discloses a system for fabricating at least a portion of a denture. The system includes a three-dimensional scanning device for scanning a surface of a denture template, and a computer-readable medium including a computer program for receiving data from the scanning device, creating a 3-dimensional model of the surface, and optionally modifying the 3-dimensional model and/or adding features to the 3-dimensional model. The system also includes a fabricator for creating the at least the portion of the denture, from a selected material, based on the 3-dimensional model. The fabricator may be a device including a lathe, or a rapid prototyping machine. There is also provided a method for fabricating at least a portion of a denture.

US2007009852 discloses a denture comprising a denture plate comprising a support member having an approximately U-shape base, a labial wall extending from said base and a lingual wall extending from said base; said base, labial wall and lingual wall forming an approximate U-shape cross-section along an imaginary vertical plane to form a channel; and a deformable member extending through the channel to separate the channel into a gum receiving section and a fitting section; and, a false teeth assembly including a plurality of false teeth secured to said base.

US2006040236 discloses a method of creating a dental restoration customized to the clinical needs of a patient comprising the steps of: preparing a patient's existing dental structures for digital modeling wherein the existing dental structures may comprise implant anchors, soft tissue, jawbone, existing teeth, and an existing denture; making a first three-dimensional digital model of the dental restoration wherein the first three-dimensional digital model comprises the implant anchors, soft tissue form, any existing teeth, and the planned position of one or more artificial teeth; creating a second three-dimensional digital model of the dental restoration wherein the second three-dimensional digital model comprises a substructure for attaching to the patient's existing dental structures and for retaining the artificial teeth; producing the substructure from the second three-dimensional digital model; positioning and securing the artificial teeth on the substructure; and securing the substructure to the patient's existing dental structures.

It remains a problem to provide an improved method for modeling and manufacturing of dentures.

SUMMARY

Disclosed is a method for modeling and manufacturing a denture for a patient, where the denture comprises a gingival part and artificial teeth, wherein the method comprises the steps of:
 providing a 3D scan comprising at least part of the patient's oral cavity;
 virtually modeling at least part of the denture using the 3D scan;
 obtaining virtual teeth to represent the artificial teeth;
 virtually modeling at least one of the virtual teeth to obtain a set of modeled virtual teeth;
 manufacturing the modeled virtual teeth in a first material;
 manufacturing the gingival part in a second material; and
 manufacturing at least part of the denture by means of computer aided manufacturing (CAM).

It is an advantage that the virtual teeth representing artificial teeth and/or the gingival may be modeled using a 3D scan comprising at least part of the patient's oral cavity. Furthermore, the virtual teeth representing the artificial teeth are virtually modeled before manufacturing of the denture. The artificial teeth may be selected from a number of virtual pre-designed teeth, and these pre-designed teeth may then be modeled to fit the patient or meet and satisfy the patient's requests and wishes. The virtual teeth may correspond to real, physical, pre-manufactured, artificial teeth. Thus the artificial teeth may be selected by the patient at the dentist's clinic either by seeing the physical artificial teeth in real life or by seeing the virtual pre-designed teeth corresponding to these physical teeth on a computer screen.

It is a further advantage that the denture can be virtually modeled, since this may provide a denture of higher quality, and the cost as well as the time needed to make the denture may be reduced. By using a 3D scan comprising the patient's oral cavity the quality of the denture may also be improved. The 3D scan comprising at least part of the patient's oral cavity comprises any teeth still present in the mouth, and it may be a 3D scan of an impression of the patient's teeth, it may be a 3D scan of a physical model of the patient's teeth, and/or it may be a 3D scan made directly in the mouth of the patient, i.e. an intra oral scan.

Providing the 3D scan may mean acquiring the 3D scan by performing the scanning, or retrieving the 3D scan from a digital file on a computer. The 3D scan may be obtained at the same time and place as the modeling and manufacturing are performed, or the 3D scan may be obtained separately from the modeling. Furthermore, the modeling and manufacturing may be performed at the same physical location, or modeling and manufacturing may be performed at different physical locations.

Furthermore, the order in which the different steps are performed can be different than the order above. However logically, the modeling steps will be performed before the manufacturing steps. But the step of obtaining virtual teeth to represent the artificial teeth may for example be performed before the step of virtually modeling at least part of the denture using the 3D scan.

The artificial teeth may be denoted a teeth part of the denture.

As well as virtual teeth represent the artificial teeth, a virtual gingival part may be defined to represent the gingival part of the denture.

When manufacturing the modeled virtual teeth, manufactured modeled teeth is obtained. It may also be denoted manufactured modeled virtual teeth.

The virtual modeling of the denture in general, and the virtual modeling of the virtual teeth and the gingival part in particular, are performed by means of computer aided designing (CAD).

Many different types of dentures exist, such as:
- full denture;
- partial denture;
- denture comprises one or more implants;
- removable denture;
- fixed denture;
- fixed partial denture;
- removable partial denture;
- bridge with or without veneering in the form of porcelain or composite;
- bar with or without implants, artificial teeth etc;
- dental prosthesis, e.g. on a bar or on teeth;
- denture comprising or being attached to an implant bar, which is adapted to be attached to the jaw bone in the mouth of a patient.

Furthermore, bar and bridge types may be standard types such as Dolder, Hader, Hybird, Canada, Wrap-around, Primary etc., and bars and bridges may be free-form design or custom shapes.

Dentures are different from restorations or prostheses, because a denture replaces missing teeth, and there will thus be artificial teeth and artificial gingival in a denture, whereas a restoration for example in the form of a crown or a bridge will not comprise artificial gingival or artificial teeth, but crowns and in the case of a bridge, one or more pontics. The processes for designing and manufacturing a denture are thus different from when designing and manufacturing restorations and prostheses.

In some embodiments the method comprises virtually modeling attachment of the artificial teeth in the gingival part.

Virtual Modeling of the Attachment of Artificial Teeth in the Gingival Part

According to an aspect, disclosed is a method for modeling and manufacturing a denture for a patient, where the denture comprises a gingival part and artificial teeth, wherein the method comprises the steps of:
- providing a 3D scan comprising at least part of the patient's oral cavity;
- virtually modeling at least part of the denture using the 3D scan;
- obtaining virtual teeth to represent the artificial teeth;
- virtually modeling at least one of the virtual teeth to obtain a set of modeled virtual teeth;
- virtually modeling attachment of the artificial teeth in the gingival part;
- manufacturing the modeled virtual teeth in a first material;
- manufacturing the gingival part in a second material; and
- manufacturing at least part of the denture by means of computer aided manufacturing (CAM).

It is an advantage that the attachment of the artificial teeth in the gingival part is virtually modeled or designed, because when also the attachment of the artificial teeth on the gingival part is virtually designed or modeled, then the whole process of designing a denture can be performed virtually or digitally, and the manufacturing process may then also be performed entirely automatic, for example without requiring any manual manufacturing or any manufacturing performed by persons.

It is an advantage to virtually design the attachment of the artificial teeth in the gingival part, since this may provide improved aesthetics and functionality of the denture, because the attachment is designed while designing the rest of the denture, and the manufacturing of the attachment may also be manufactured while the rest of the denture is manufactured.

It is an advantage also to virtually design the attachment of the artificial teeth in the gingival part as well as designing the other parts of the denture, since virtually designing the attachment may provide a better, firmer, stronger, more solid, robust and reliable attachment of the artificial teeth.

It is an advantage that in the design process it is ensured that the designed teeth actually can also be physically attached in the designed gingival, since the design of the attachment can be visually and computationally checked and verified that it can physically be implemented and executed in the manufactured denture.

Attachment Means and Structures

In some embodiments the method comprises virtually modeling means for attachment of the artificial teeth in the gingival part.

In some embodiments the method comprises virtually modeling physical structures for attaching the artificial teeth in the gingival part.

In some embodiments the method further comprises selecting predesigned physical structures in a digital library for attaching the artificial teeth in the gingival part.

Methods for Virtually Modeling the Attachment of Artificial Teeth in the Gingival Part In some embodiments the virtual modeling of the attachment of the artificial teeth in the gingival part comprises mathematically subtracting a first shape from a second shape.

In some embodiments the first shape is the artificial teeth and the second shape is the gingival part.

In some embodiments the virtual modeling of the attachment of the artificial teeth in the gingival part comprises offsetting at least a part of the artificial teeth and/or at least part of the gingival part.

In some embodiments the virtual modeling of the attachment of the artificial teeth in the gingival part comprises a cavity operation.

In some embodiments the cavity operation comprises subtracting the shape of the artificial teeth which is configured for being arranged in the gingival from the gingival part.

It is an advantage to virtually design the artificial teeth and the gingival part such that the area in the gingival part where the artificial teeth shall be arranged is designed or modeled to match the area on the artificial teeth which shall be arranged in the gingival part. For ensuring an effective and stable attachment the shape of the area in the gingival part where the artificial teeth are configured to be arranged may match, fit, correspond, resemble the shape of the area on the artificial teeth which are configured to be arranged in the gingival part. Thus the adjacent 3D surfaces of the contact area on an artificial tooth and of the contact area in the gingival part may be designed to exactly match or fit each other.

The contact area on the artificial tooth/teeth may be designed and then the design may be copied or transferred to the contact area in the gingival part. Alternatively, the contact in the gingival part may be designed and then the design may be copied or transferred to the contact area on the artificial tooth/teeth.

Alternatively and/or additionally, a pre-designed, standard contact area may be selected from a digital library in a computer software program, and the design of this selected contact area may then be applied or transferred to the contact area in the gingival part and/or to the contact area on the artificial teeth.

Holes in Gingival Part to Receive Teeth

In some embodiments the method further comprises modeling and manufacturing holes in the gingival part to receive the manufactured teeth.

The Physical Design of the Attachment

In some embodiments the attachment of the artificial teeth in the gingival part is obtained by means of performing undercuts in the gingival part and press-fitting the artificial teeth into the holes and undercuts in the gingival part.

In some embodiments the attachment of the artificial teeth in the gingival part is obtained by means of interlocking features.

In some embodiments the interlocking features are arranged in the holes in the gingival part and/or in the area of the artificial teeth which is adapted to be arranged in the holes in the gingival part.

In some embodiments the interlocking features are ball-shaped.

In some embodiments the interlocking features are adapted to be pushed in such that they align with the surface they are arranged in, and where the interlocking features are then adapted to be pushed out when the artificial teeth are arranged in the holes in the gingival part for locking the artificial teeth in the gingival part.

In some embodiments the interlocking features are adapted to be pushed in such they align with the surface they are arranged in, when pressure is applied on the interlocking features, and when pressure is relieved from the interlocking features they are adapted to be pushed out.

In some embodiment the attachment of the artificial teeth in the gingival part is performed by means of gluing the artificial teeth into the holes of the gingival part.

In some embodiments the artificial teeth are attached in the gingival part by means of providing a bore in the area of the artificial teeth which is adapted to be arranged in the hole in the gingival part, and arranging a bar in the bore, where the bar is adapted to extend to the gingival part for retaining the artificial teeth in the gingival part.

In some embodiments the artificial teeth are attached in the gingival part by fastening means.

In some embodiments the fastening means are screws.

Manufacturing the Attachment

In some embodiments the method further comprises manufacturing attachment means for attaching the artificial teeth in the gingival part.

According to an aspect of the present invention a method is disclosed for modeling a denture for a patient, where the denture comprises a gingival part and artificial teeth, wherein the method comprises the steps of:

providing a 3D scan comprising at least part of the patient's oral cavity;
virtually modeling at least part of the denture using the 3D scan;
obtaining virtual teeth to represent the artificial teeth;
virtually modeling at least one of the virtual teeth to obtain a set of modeled virtual teeth.

Furthermore, according to an aspect of the present invention, a method is disclosed for manufacturing a denture for a patient, where the denture comprises a gingival part and artificial teeth, where a 3D scan comprising at least part of the patient's oral cavity is provided, where at least part of the denture is virtually modeled using the 3D scan; where virtual teeth are obtained to represent the artificial teeth; where at least one of the virtual teeth is virtually modeled to obtain a set of modeled virtual teeth, where the method comprises the steps of:

manufacturing the modeled virtual teeth in a first material;
manufacturing the gingival part in a second material; and
manufacturing at least part of the denture by means of computer aided manufacturing (CAM).

In some embodiments the artificial teeth are manufactured in a synthetic polymer material, such as acrylic.

Acrylic means a material consisting of or comprising or derived from acrylic.

In some embodiments the first and the second material are the same.

In some embodiments the first and the second material are different.

In some embodiments the method further comprises obtaining the virtual teeth by algorithmic shaping.

It is an advantage since the fitting and aesthetics of the artificial teeth may be improved, when the virtual teeth are obtained by algorithmic shaping. The algorithmic shaping may be based on the existing teeth, gingival etc. in the patient's mouth.

In some embodiments the method further comprises obtaining the virtual teeth by selection from among a number of virtual, pre-designed teeth. Thus when virtually modeling at least one of the selected, virtual, pre-designed teeth, a set of adjusted pre-designed teeth will be obtained.

In some embodiments the method further comprises selecting the pre-designed teeth from a library of template teeth.

The library may be the user's or operator's own library, a library from certain manufacturers of artificial teeth etc. Alternatively and/or additionally the artificial teeth are from a user's own design of teeth for a denture, from an existing restoration etc.

In some embodiments the method further comprises selecting the pre-designed teeth based on shape and/or color.

In some embodiments the virtual teeth correspond to pre-manufactured teeth.

Thus the virtual teeth exist as or have corresponding pre-manufactured teeth. The virtual teeth and the corresponding physical pre-manufactured artificial teeth may be from a manufacturer of artificial teeth, such as Ivoclar, Heraeus, Dentsply, Merz, Vita etc.

Thus the result of the virtual modeling of the virtual teeth will be manufactured by physically modeling the pre-manufactured teeth. This may be performed using a CAD-CAM milling or grinding machine.

Alternatively, if using e.g. a ceramic system such as e.max, all the artificial teeth are manufactured from scratch, and no pre-manufactured teeth are used. The teeth will then be fully customizable teeth based on a design. Thus in some embodiments the artificial teeth are adapted to be manufactured from scratch using no pre-manufactured teeth.

In some embodiments at least the pre-manufactured teeth are made of a material which is adapted to be grinded and/or milled.

In some embodiments the method further comprises automatic grinding or milling the pre-manufactured teeth according to the modeled virtual teeth by means of a CAM machine.

Alternatively, pre-manufactured teeth may be used directly in the denture without modifying them, if the design of the pre-manufactured teeth fit well to the patient. However, normally the virtual teeth will be modeled somehow in order to fit the present case.

In some embodiments the method further comprises manufacturing the modeled virtual teeth from pre-manufactured teeth corresponding to the virtual teeth.

In some embodiments the method further comprises manufacturing the modeled virtual teeth from blanks.

The blanks may be e.max ceramic blanks or other suitable blanks.

In some embodiments the method further comprises manufacturing the modeled virtual teeth by printing.

It is an advantage that the teeth of the denture may be manufactured by means of 3D printing, since 3D printing may provide that the artificial teeth are of good quality both aesthetically and functionally. Furthermore, if both the teeth part and the gingival part of the denture are printed, then the manufacturing of the denture may be performed fast and with a good result. Even though both the teeth part and the gingival part are printed, they may be printed in different materials, e.g. a hard material for the teeth part and a soft material for the gingival part, and/or in different colors, such that the teeth part are printed in a white material and the gingival part are printed in a pink/red material resembling the natural color of the gingival.

In some embodiments the method further comprises providing the virtual teeth to have a size so big, that during manufacturing of the modeled virtual teeth, material is only removed from and not added to the corresponding pre-manufactured teeth.

It is an advantage since hereby a grinding or milling machine can be used, since material should only be removed from the pre-manufactured teeth, and a milling or grinding machine is adapted to cut away material.

When modeling the gingival part of the denture, different things are taken into account. When a patient has no or only some teeth in the mouth, the gingival and the underlying bone structure will disintegrate, where there are no teeth. Thus the gingival part of the denture must be bigger in those areas where the patient has been without teeth for a while, since the gums have collapsed in these areas.

In some embodiments, the method further comprises modeling the gingival part based on a template gingival.

In some embodiments the method further comprises modeling the gingival part based on a determined occlusal plane.

The occlusal plane may be determined based on the position of the retromolar space of the mouth and on the position corresponding to a center point between the two lower central teeth. The occlusal plane may furthermore be determined based on other specific points, teeth, distances etc of the patient's mouth.

In some embodiments the method further comprises determining where the edge of the gingival part should end at the existing, physiological gingival. This may be determined based on a template gingival or it may be marked manually. The edge of the gingival part should end at a place such that it looks natural.

In some embodiments the method further comprises determining where the gingival part should end at the teeth.

This may be determined based on different templates, such as a low-gingival template, a high-gingival template and a normal-gingival template. It may also be marked manually on the teeth. The edge of the gingival part should end at a place such that it looks natural.

In some embodiment the method further comprises using offsetting, lofting and smooth transitioning to model the gingival part relative to the existing physiological gingival and the virtual teeth.

Thus points may be marked on the teeth for indicating that the gingival part should end there, a first offset of the gingival part from the existing gingival may be determined, a second offset of the gingival part from the teeth may be determined, a smooth transition connecting the first offset from the existing gingival and the second offset from the teeth may be performed using a lofting operation.

Offsetting may be defined as that an offset within an array or other data structure object is an integer indicating the distance or displacement from the beginning of the object up until a given element or point.

Lofting is a drafting technique to draw curved lines. The technique can be used to perform bending of an object, in this case a virtual object, so that it passes over three non-linear points and scribing the resultant curved line, or plotting the line using computers or mathematical tables.

In some embodiments the method further comprises offsetting the gingival part around the virtual teeth.

By offsetting the gingival part around the virtual teeth and finally around the manufactured teeth, the gingival part will look more natural since this offsetting corresponds to how the real physiological gingival looks around the teeth.

In some embodiments the method further comprises applying stipple wax pattern on the gingival part.

By applying stipple wax pattern the gingival part will look more natural. However it may be more difficult to clean the denture when there are offsets and stipple wax pattern because the gingival part will be more bulky, and therefore only the front part of the gingival part may be applied with the stipple wax pattern, while the part of the gingival hidden by the lips and the mouth may be smooth for easier cleaning.

In some embodiments the method further comprises arranging the position of the virtual teeth in the gingival part based on predetermined rules or criteria.

For example the vertical distance between where the real gingival ends in the mouth and where the teeth ends can be a certain distance.

Furthermore, mirroring and symmetry may be used to model the gingival part as well as the teeth.

In some embodiments the method further comprises that at least the gingival part of the denture is manufactured by means of 3D printing.

In some embodiments the method further comprises that at least the gingival part is manufactured by means of milling.

It is an advantage since milling may be easiest to use when undercuts should be manufactured on the gingival.

In some embodiments the method further comprises modeling and manufacturing holes in the gingival part to receive the manufactured teeth.

In some embodiments the method further comprises manufacturing the gingival part and the manufactured teeth separately.

In some embodiments the method further comprises assembling the manufactured teeth and the gingival part automatically after the manufacturing, whereby the manufactured teeth are arranged into the corresponding holes in the gingival part.

In some embodiments the method further comprises manufacturing the modeled virtual teeth and the gingival part collectively.

A collective manufacturing may be performed if both the teeth part and the gingival part of the denture are manufactured by means of for example milling or 3D printing.

In some embodiments the method further comprises providing the virtual teeth to have a size so big, that during modeling of the virtual teeth, material is only removed from and not added to the virtual teeth.

It is an advantage because hereby when the teeth are manufactured from pre-manufactured teeth, the pre-manufactured teeth can be adjusted in a milling or grinding machine, because material should only be removed.

In some embodiments the virtual teeth are a composed set of teeth comprising a number of teeth arranged spatially relative to each other forming a high functional and aesthetic composition.

A high functional composition or combination may be a composition with a good occlusion, bite etc. A high aesthetic composition may be a composition which is visually pleasing.

In some embodiments the method further comprises collectively modifying one or more parameters of the teeth in the composed set of teeth.

In some embodiments the denture is adapted to be attached to dental implants and/or on dental implant bars or bridges.

The dental implant bars or bridges may be the primary structure, and the denture may be the secondary or tertiary structure.

Alternatively, the denture is adapted to be supported by existing teeth and/or the real gums in the patient's mouth.

In some embodiments the method further comprises modeling the denture and the dental implants and/or dental implant bar or bridge to fit each other.

In some embodiments the method further comprises modeling the attachment means for attaching the denture and the dental implants and/or dental implant bar or bridge to fit each other.

In some embodiments the method further comprises modeling pins on the dental implant bridge and corresponding holes in the denture to fit each other.

The pins may be virtually moved to fit in the virtual teeth of the denture. The pins may be free-form shaped or selected from a library or from default templates. The holes may be generated automatically based on the arrangement of the pins. There may also be a cement space in the hole where the pin does not reach down. Pins may be used in a denture for providing extra strength of the denture.

In some embodiments the method further comprises obtaining the dental implant pins and automatically generating the corresponding holes in the denture to fit the dental implant pins.

The pins may be modeled, selected from a library of dental implant pin templates, or selected from among a number of default pin templates.

In some embodiments the holes in the denture are manufactured according to the corresponding pins in the bridge.

In some embodiments the method further comprises modeling dental implant pins and holes in the denture based on holes in the pre-manufactured teeth.

The holes may be standard holes in the pre-manufactured teeth, they may be modeled, selected from a library of holes templates, or selected from among a number of default holes templates.

In some embodiments the pins in the bridge are manufactured according to the corresponding holes in the gingival.

In some embodiments the denture is adapted to be attached to a partial removable framework.

Thus the denture may be attached at least partly to a partial removable framework, and e.g. partly to existing teeth in the mouth.

In some embodiments the method further comprises collectively modeling the partial removable framework and the denture comprising the manufactured teeth and the gingival part.

In some embodiments when the gingival part of the denture is manufactured separately by 3D printing, then the method further comprises separating the gingival part and/or the partial removable framework into at least two pieces, such that the gingival part and the partial removable framework are adapted to be assembled and attached to each other.

In some embodiments the method further comprises virtually blocking out the space between the partial removable framework and the existing gingival.

The space may be virtually blocked out such that when manufacturing the gingival part based on the CAD design, the gingival part will not extend between the partial removable framework and the real gingival.

When manufacturing a denture, traditionally a try-in is made and tested in the patient's mouth before producing the final denture. The reason for this is that the material which the denture is made of is a hard material for ensuring maintenance of the shape, but when testing and adjusting it is easier to use a soft material, and the try-in is thus made in a deformable material.

In some embodiments the method further comprises the steps of:
  manufacturing a try-in comprising at least a try-in gingival;
  testing the try-in in the patient's mouth;
  if the try-in does not fit, adjusting the try-in to fit in the patient's mouth.

The try-in may also comprise try-in teeth. Thus the try-in may also be denoted a try-in denture, a try-in gingival, try-in teeth etc.

In some embodiments the method further comprises printing the try-in gingival in a deformable material, such as wax.

In some embodiments the method further comprises scanning the try-in after testing in the patient's mouth and optional adjustment.

In some embodiments the method further comprises automatically detecting the changes in the scan of the try-in after the adjustments and modifying the denture design based on this.

This may be performed by overlaying the first unmodified design or scan of the try-in with the second modified scan or design of the try-in, and/or morphing the first unmodified design or scan to the second modified design or scan, segmenting the scan into the teeth and the gingival, and then move the gingival and/or the teeth in the two scans or designs relative to each other for providing a correct overlaying. Then the new denture design can be performed.

In some embodiments the try-in gingival is made in a material which is subject to hardening.

In some embodiments after the try-in has been tested in the patient's mouth and optionally adjusted, the method further comprises hardening the try-in gingival, and providing the try-in gingival to be at least part of the denture.

In some embodiments the method further comprises hardening the try-in by means of light radiation.

In some embodiments after the try-in has been tested in the patient's mouth and optionally adjusted, a gingival part is modeled based on the optionally adjusted try-in and printed in a hard material.

In some embodiments the try-in comprises the manufactured modeled teeth.

In some embodiments the manufactured modeled teeth used in the try-in are also inserted in the final denture.

Thus only one set of manufactured artificial teeth are manufactured since the teeth are used both in the try-in and in the final denture.

In some embodiments at least one of the manufactured modeled teeth used in the try-in is replaced with a new manufactured modeled tooth, when inserted in the final denture.

If one or more of the manufactured artificial teeth appears not to fit in the denture after testing them in the try-in, those teeth not fitting will be replaced by manufactured remodel teeth.

In some embodiments the method further comprises using a dynamic virtual articulator for simulating occlusion of the teeth set comprising the modeled denture and any teeth still present in the patient's mouth.

In some embodiments the modeled denture and any teeth still present in the patient's mount comprise a virtual upper jaw and a virtual lower jaw of the teeth set.

In some embodiments the method further comprises positioning a virtual alignment plane relative to the virtual upper jaw and the virtual lower jaw.

In some embodiments the virtual alignment plane is fixed relative to the virtual articulator.

In some embodiments the virtual alignment plane is a default occlusal plane.

In some embodiments the virtual alignment plane is plane or curved.

In some embodiments the method further comprises automatic movement of the virtual alignment plane relative to the movement of the virtual teeth in the denture, when the virtual teeth are being modeled.

In some embodiments one or more of the steps of the method is computer-implemented.

Furthermore, the present invention relates to a computer program product comprising program code means for causing a data processing system to perform the method above when said program code means are executed on the data processing system, and a computer program product comprising a computer-readable medium having stored thereon the program code means.

The present invention relates to different aspects including the method described above and in the following, and corresponding methods, devices, systems, uses, and/or product means, each yielding one or more of the benefits and advantages described in connection with the first mentioned aspect, and each having one or more embodiments corresponding to the embodiments described in connection with the first mentioned aspect and/or disclosed in the appended claims.

In particular, disclosed herein is a system for modeling and/or manufacturing a denture for a patient, where the denture comprises a gingival part and artificial teeth, wherein the system comprises:
- means for providing a 3D scan comprising at least part of the patient's oral cavity;
- means for virtually modeling at least part of the denture using the 3D scan;
- means for obtaining virtual teeth to represent the artificial teeth;
- means for virtually modeling at least one of the virtual teeth to obtain a set of modeled virtual teeth;
- means for manufacturing the modeled virtual teeth in a first material;
- means for manufacturing the gingival part in a second material; and
- means for manufacturing at least part of the denture by means of computer aided manufacturing (CAM).

In particular, disclosed herein is a system for modeling and manufacturing a denture for a patient, where the denture comprises a gingival part and artificial teeth, wherein the system comprises:
- means for providing a 3D scan comprising at least part of the patient's oral cavity;
- means for virtually modeling at least part of the denture using the 3D scan;
- means for obtaining virtual teeth to represent the artificial teeth;
- means for virtually modeling at least one of the virtual teeth to obtain a set of modeled virtual teeth;
- means for virtually modeling attachment of the artificial teeth in the gingival part;
- means for manufacturing the modeled virtual teeth in a first material;
- means for manufacturing the gingival part in a second material; and
- means for manufacturing at least part of the denture by means of computer aided manufacturing (CAM).

Disclosed is also a device for modeling and/or manufacturing a denture for a patient, where the denture comprises a gingival part and artificial teeth, wherein the device comprises:
- means for providing a 3D scan comprising at least part of the patient's oral cavity;
- means for virtually modeling at least part of the denture using the 3D scan;
- means for obtaining virtual teeth to represent the artificial teeth;
- means for virtually modeling at least one of the virtual teeth to obtain a set of modeled virtual teeth;
- means for manufacturing the modeled virtual teeth in a first material;
- means for manufacturing the gingival part in a second material; and
- means for manufacturing at least part of the denture by means of computer aided manufacturing (CAM).

According to another aspect of the invention a fixture apparatus is disclosed for retaining a blank from which at least manufactured teeth of a denture are adapted to be manufactured according to any of the preceding claims.

It is an advantage since hereby the blank is arranged in the fixture in a known position relative to the grinding/milling machinery.

BRIEF DESCRIPTION OF THE DRAWINGS

The above and/or additional objects, features and advantages of the present invention, will be further elucidated by the following illustrative and non-limiting detailed description of embodiments of the present invention, with reference to the appended drawings, wherein:

FIGS. 2a) to 2c) show examples of manufactured dentures.

FIGS. 6a) and 6b) show examples of implant bridges.

FIG. 7 shows an example of combination of different CAD modeling for a set of teeth.

DETAILED DESCRIPTION

In the following description, reference is made to the accompanying figures, which show by way of illustration how the invention may be practiced.

Figure 1:
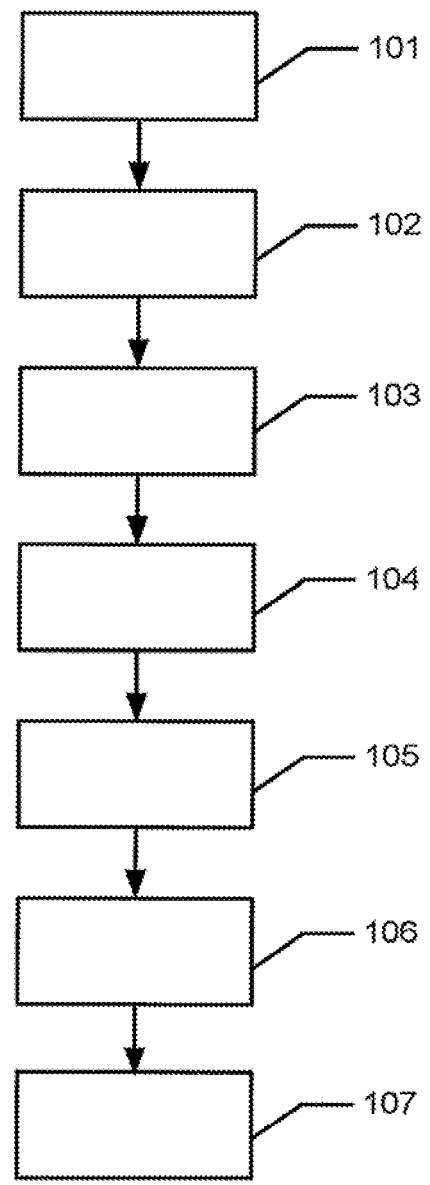
FIG. 1 shows an example of a flow chart of the method.

FIG. 1 shows an example of a flow chart of the method for computer-aided modeling and computer-aided manufacturing of a denture comprising a gingival part and artificial teeth.

In step 101 a 3D scan comprising at least part of the patient's oral cavity os provided.

In step 102 at least part of the denture is virtually modeled using the 3D scan.

In step 103 virtual teeth is obtained to represent the artificial teeth.

In step 104 at least one of the virtual teeth is virtually modeled to obtain a set of modeled virtual teeth.

In step 105 the modeled virtual teeth is manufactured in a first material.

In step 106 the gingival part is manufactured in a second material.

In step 107 at least part of the denture is manufactured by means of computer aided manufacturing (CAM).

FIG. 2 shows examples of manufactured dentures.

FIG. 2a) shows pictures of a denture 201 which is, or is a part of, or comprises a partial denture. The partial denture 201 comprises a framework 206 and a gingival part 203 and a teeth part comprising artificial acrylic teeth 205.

In the top image, the partial denture is arranged next to a model of the patient's present teeth, and the denture is seen from below, i.e. from the side pointing towards the palate.

In the bottom image, the partial denture is arranged on the model of the patient's teeth, and the denture is seen from above, i.e. from the side pointing towards the surroundings when the denture is arranged in the mouth of the patient.

FIG. 2b) shows pictures of an upper denture 201 and a lower denture, which are both partial dentures. The partial dentures 201 comprise a framework 206 and a gingival part 203 and the top image also shows a teeth part comprising artificial acrylic teeth 205.

In the top image, the partial dentures are arranged on the models of the patient's present teeth, and the dentures are seen from above or from the frontside.

In the bottom image, the partial dentures are arranged next to the models of the patient's teeth, and the dentures are seen from below or from the backside. In the bottom image the dentures are shown without the artificial teeth or the veneering of the metal framework.

FIG. 2c) shows pictures of a denture 201 which is a full maxillary denture, i.e. a denture for the upper arch. The denture 201 comprises a gingival part 203 and a teeth part comprising artificial teeth 205 made of acrylics.

In the top image, the partial denture is arranged on the model of the patient's present teeth, and the denture is seen from above or from the frontside.

In the bottom image, the partial denture is arranged next to the model of the patient's teeth, and the denture is seen from below or from the backside.

The denture 201 shown in FIG. 2c) is a removable denture, and it is not attached to the mouth by any attachment means when in use, so the patient can at any time remove the denture. The denture 201 of FIG. 2c) is held in place in the patient's mouth by means of friction, suction, negative pressure etc.

The dentures 201 of FIG. 2a) and FIG. 2b) may be removable for the patient, however alternatively the dentures may be attached to the existing teeth by some attachment means, which only the dentist should manage.

InteraDent Zahntechnik GmbH in Lübeck, Germany has provided the images of the different dentures shown in FIG. 2.

FIG. 3 shows examples of virtual modeling of dentures.

Figure 3A:
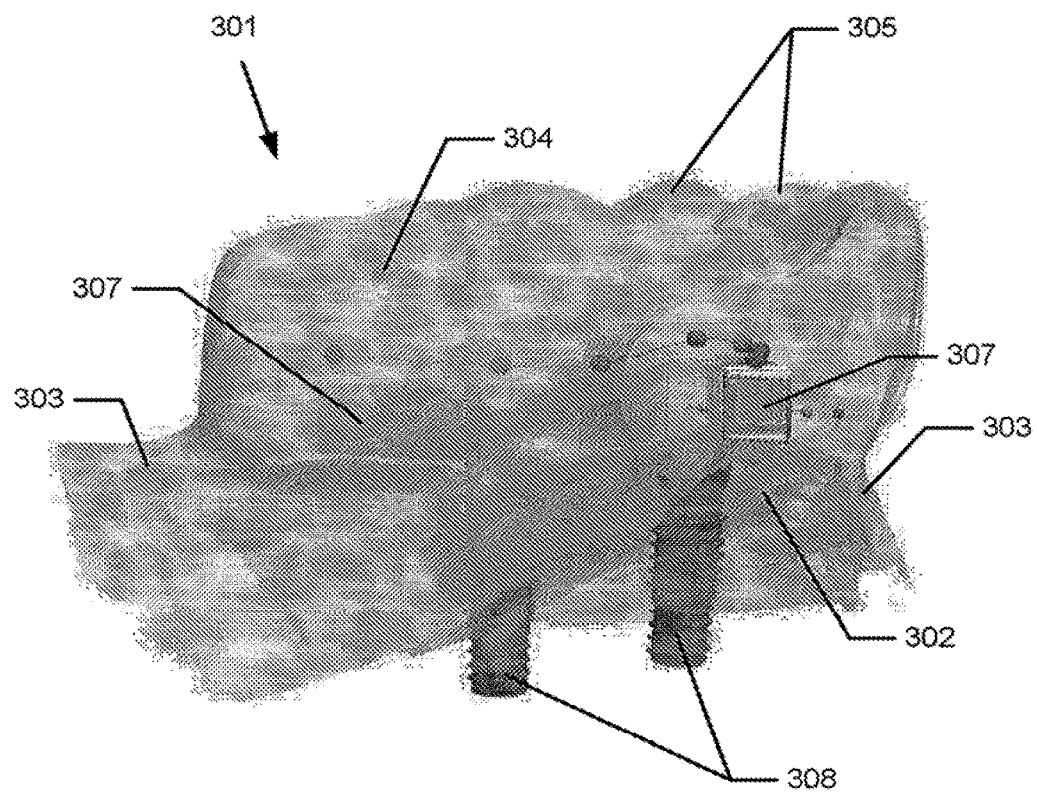
FIGS. 3a) and 3b) show examples of virtual modeling of dentures.

FIG. 3a) shows an example of virtual modeling of an implant bar for implants and denture.

The virtual denture 301 comprises a virtual teeth part 304 comprising virtual teeth 305, and a virtual gingival part 303. Inside the virtual denture 301 which is transparent, a virtual implant bar 307 is seen and marked with dots above it. A number of virtual implant screws 308 are also seen sticking out underneath the denture 301. The implant screws 308 are attached to the implant bar 307. A part of a scan 302 of the patient's jaw is also seen inside the denture 301.

The implant bar 307 is modeled for optimal fit to the denture 301 and implants 308 using virtual tools in the computer aided drawing (CAD) software. Virtual measurements can be performed to validate space and distances of the denture 301, the scan 302, the implant bar 307, the implants screws 308 etc. The connection from the implant bar 307 to the implants 308 can be shaped as a cylindrical extension, as a freeform emergence profile etc.

Figure 3B:
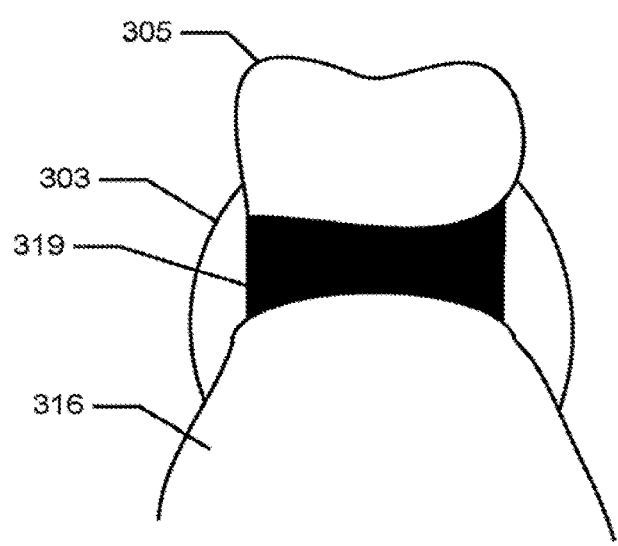

FIG. 3b) shows an example of virtual modeling of a removable denture.

A virtually modeled tooth 305 in a partial removable framework is arranged with a distance to the existing gingival 316, and the space 319 between the tooth and the existing gingival is virtually blocked out for avoiding having the denture material between the teeth and the existing gingival when the manufactured denture is worn by the patient. The gingival part 303 is modeled such that the tooth 305 is attached in the gingival part 303.

FIG. 4 shows examples of different implant bars.

Figure 4A:
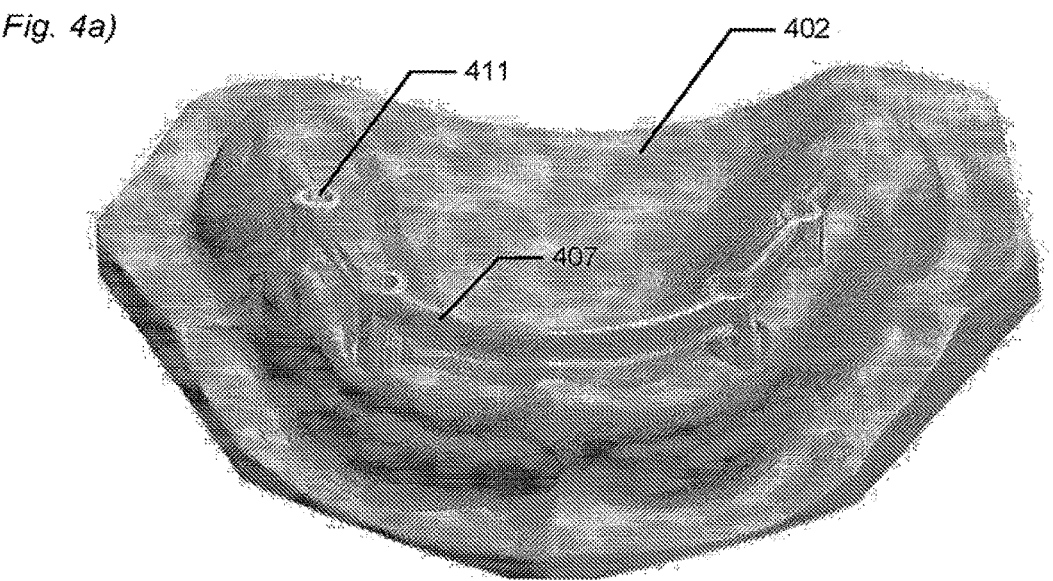
FIGS. 4a) to 4c) show examples of different implant bars.

FIG. 4a) shows an example of an implant bar 407 for a full denture (not shown). The denture may be a removable denture, i.e. it may be removably attached to the implant bar 407 by means of attachments in the form of e.g. clips (not shown) which can be snapped on and off the implant bar 407. The implant bar 407 comprises holes 411 for receiving implants.

Figure 4B:
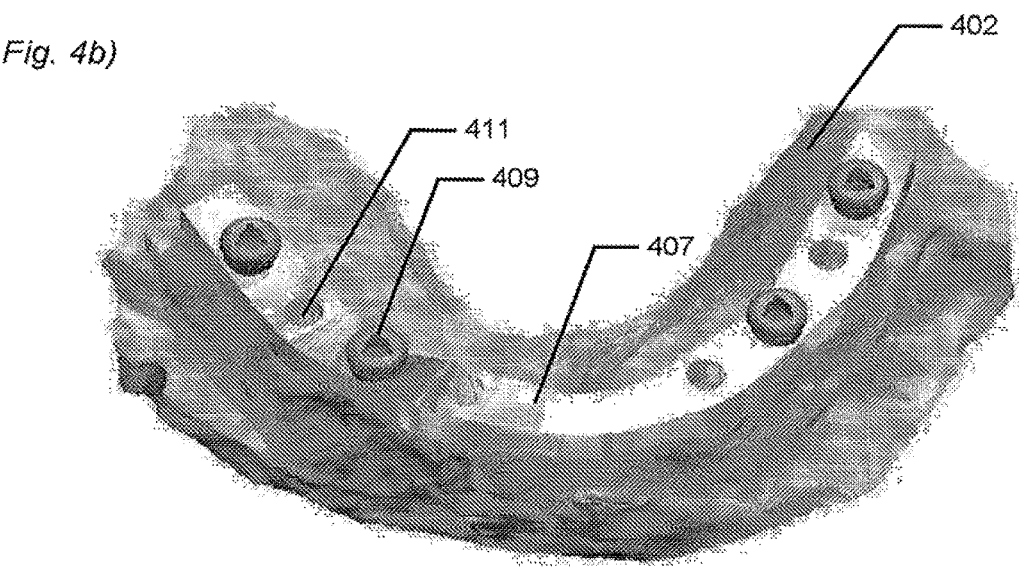

FIG. 4b) shows an example of an implant bar 407 for a full denture (not shown). The denture may be a removable denture, i.e. it may be removably attached to the implant bar 407 by means of attachments 409 in the form of locators present on both the denture and on the implant bar 407, where the locators 409 provides that the denture can be clicked on and off the implant bar 407.

The implant bar 407 comprises holes 411 for receiving implants.

Figure 4C:
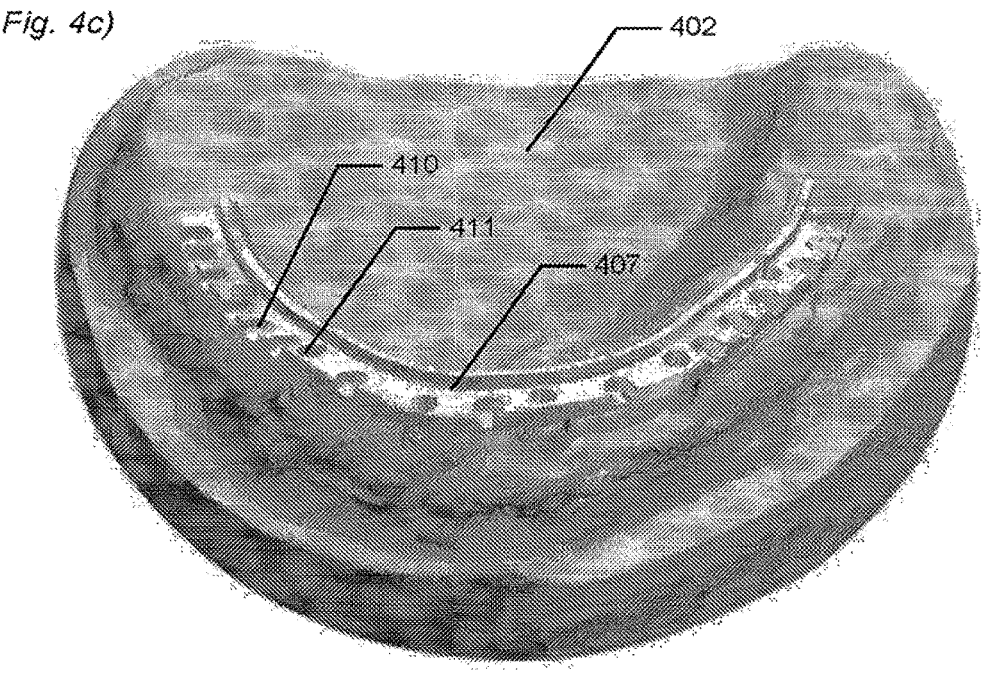

FIG. 4c) shows an example of an implant bar 407 for a full denture (not shown). The denture may be a fixed denture, i.e. it may be fixedly attached to the implant bar 407 e.g. by gluing part of the denture into the retention holes 410 in the implant bar 407. This may be performed by using acrylics in the denture, and the soft acrylics from the denture will then run into the retention holes 410 of the implant bar 407 and thereby attaching the denture to the implant bar 407.

The implant bar 407 comprises holes 411 for receiving implants.

FIG. 5 shows examples of different attachment types.

Figure 5A:
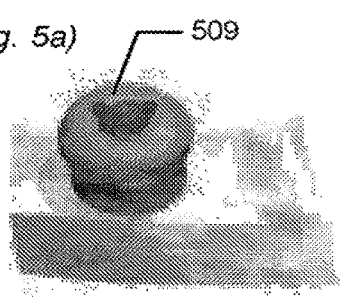
FIGS. 5a) to 5c) show examples of different attachment types.

FIG. 5a) shows an attachment in the form of a locator 509. The locator 509 may comprise a male part on e.g. the implant bar and a female part on e.g. the denture or vice versa, and the male part and the female part may work as a button.

Figure 5B:
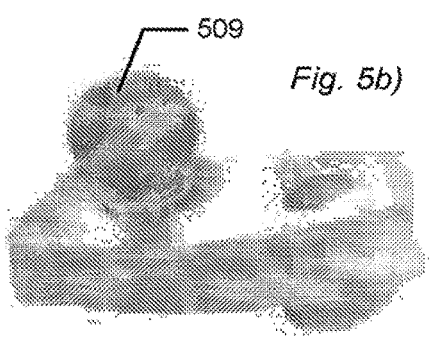

FIG. 5b) shows an attachment in the form of a ball attachment 509.

Figure 5C:
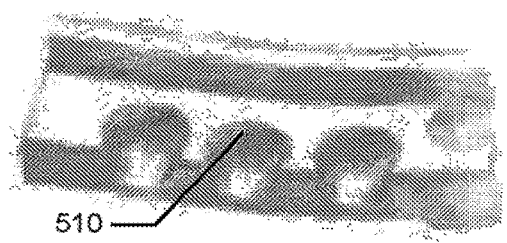

FIG. 5c) shows an attachment in the form of retention holes 510.

Another type of attachment may be a slide attachment, however any kind of attachment from a CAD library may be used.

When modeling the denture and implant, the different kinds of attachments can be added anywhere on the implant bar, and the attachments can then be rotated and translated for fine-adjustment of their position and angles.

FIG. 6 shows examples of implant bridges.

FIG. 6a) shows an example of an implant bridge 607 onto which a full denture is adapted to be arranged. On the side opposite to where the denture should be attached, the implant bridge 607 comprises protrusions 612 from holes for receiving implants (not shown).

FIG. 6b) shows an example of an implant bridge 607 comprising pins 613 where each pin is adapted to receive an artificial tooth having a hole in it for fitting over the pin, or where the pin is adapted to be covered by veneering in the form of e.g. ceramics or composite material for resembling teeth. Thus in this case the denture may be defined as comprising the artificial teeth attached onto the pins, or the denture may be defined as the veneering resembling teeth. On the side opposite to the pins 613, the implant bridge 607 comprises protrusions 612 from holes for receiving implants (not shown).

An original wax-up bar design may be scanned for remodeling the implant bar in a new material to create a digitized file that is suitable for e.g. copy milling. Adjustments to the digitized model can be applied to achieve the optimal copy milling result.

FIG. 7 shows an example of combination of different CAD modeling for a set of teeth.

All restorations may be designed in the same modeling session using embodiments of the present method. When all restorations are modeled in the same session the efficiency and clinical result will be improved.

FIG. 7 shows a standard bridge 714, full anatomical crowns 715, an implant bridge 707 and implants 708. A denture should also be modeled using CAD and after manufacturing be attached to the implant bridge 707 and e.g. on the standard bridge 714. Alternatively, veneering can be applied to the standard bridge to make it an anatomical bridge, e.g. veneering in the form of porcelain.

FIG. 8 shows an example of a how a denture and a partial removable framework are attached to each other.

Figure 8A:
FIGS. 8a) and 8b) show an example of a how a denture and a partial removable framework are attached to each other.

FIG. 8a) shows a partial removable framework 806 with retention grid and holes 817 but without artificial teeth or gingival attached.

Figure 8B:
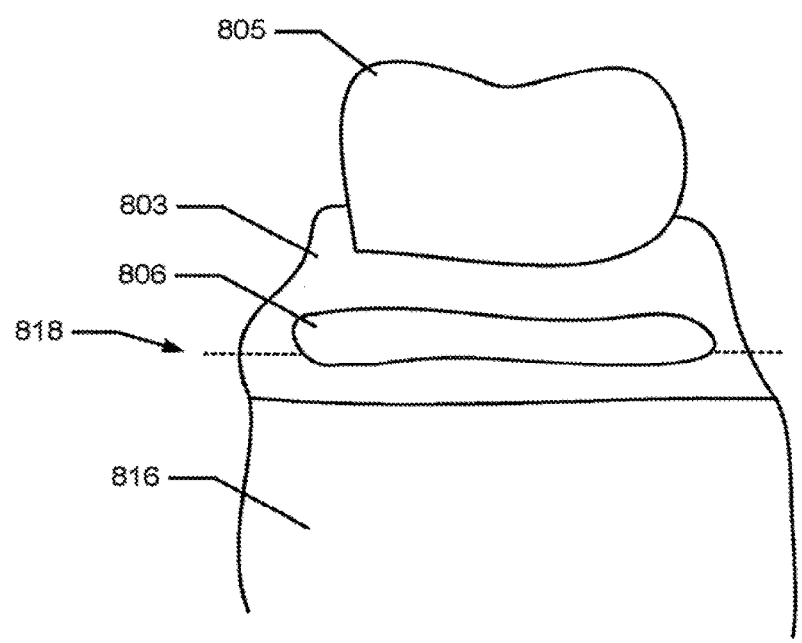

FIG. 8b) shows a cross section of a denture with a partial removable framework, for example as those seen in FIGS. 2a) and 2b). The partial removable framework 806 is embedded in the gingival part 803, since the gingival part 803 is both present above and below the framework 806. An artificial tooth 805 is arranged in the gingival part, and the gingival part 803 rests on the patient's real physiological gingival 816.

If the gingival part 803 is poured in silicone, then the liquid silicone can flow into the holes of the retention grid 817 in the framework 806. But if the gingival part 803 is printed, then there is no liquid silicone to flow into the holes of the retention grid 817. For the framework 806 and the gingival part 803 to be attached to each other, the gingival part 803 may then be separated as indicated by the separation line 818 into two or more pieces which can then be assembled around the framework 806. The separation line(s) 818 can be at other places in the gingival part 803, e.g. vertical instead of horizontal etc. Alternatively and/or additionally, the framework 806 including the retention grid 817 can be separated into two or more pieces.

FIG. 9 shows examples of modeling the gingival part.

Figure 9A:
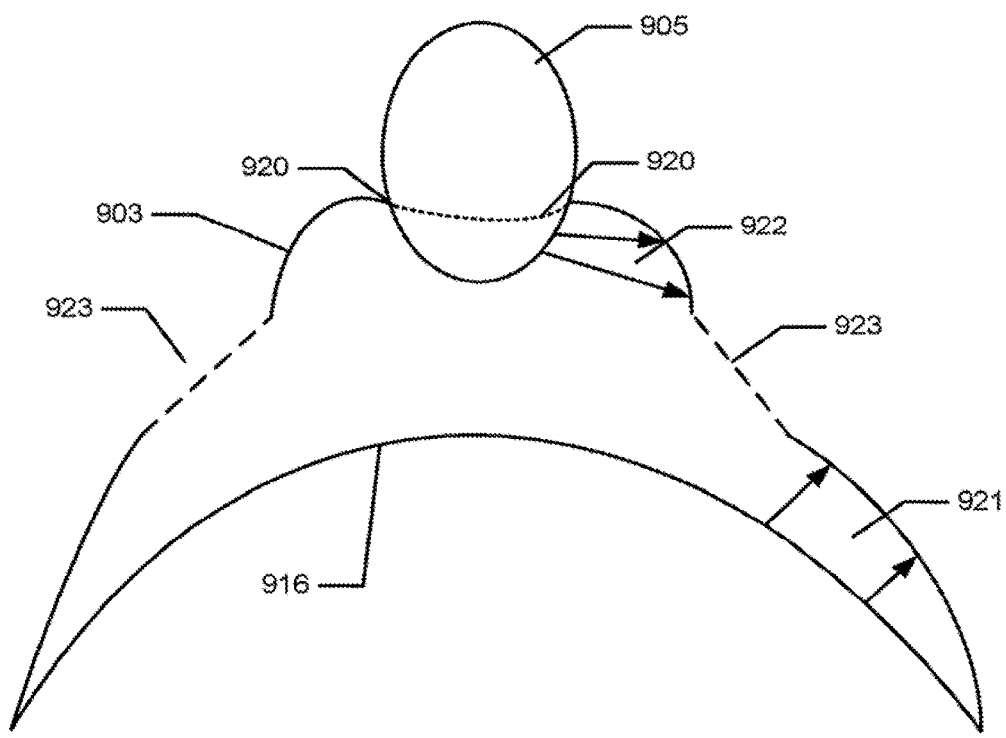
FIGS. 9a) and 9b) show examples of modeling the gingival part.

FIG. 9a) shows points 920 marked on the teeth 905 for indicating that the gingival part 903 should end there. A first offset 921, marked by arrows, of the gingival part 903 from the existing gingival 916 may be determined, an second offset, marked by arrows, 922 of the gingival part 903 from the teeth 905 may be determined, a smooth transition 923 connecting the first offset 921 from the existing gingival 916 and the second offset 922 from the teeth may be performed using a lofting operation.

Figure 9B:
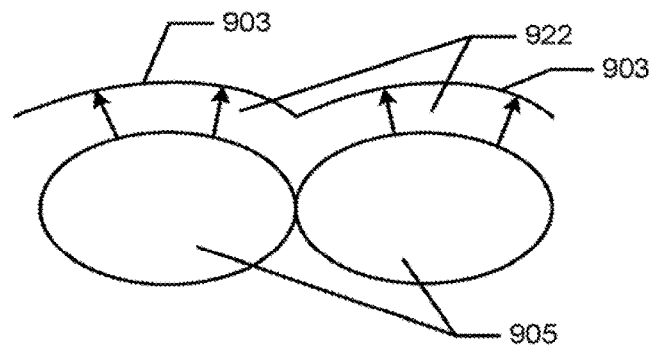

FIG. 9b) shows an example of offsetting 922, marked by arrows, the gingival part 903 around the virtual teeth 905. By offsetting the gingival part 903 around the virtual teeth 903 and finally around the manufactured teeth, the gingival part 903 will look more natural since this is how the physiological gingival looks.

FIG. 10 shows examples of attachment of the artificial teeth in the gingival part.

Figure 10A:
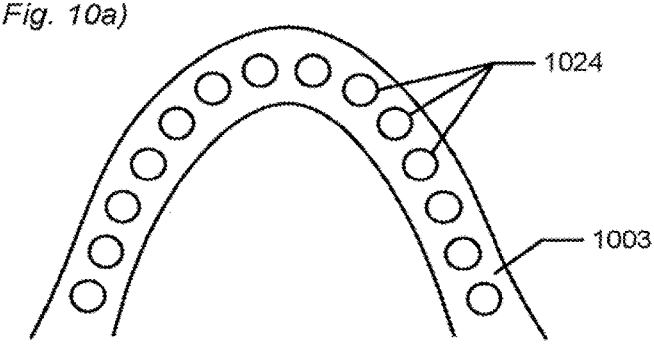
FIGS. 10a) to 10f) show examples of attachment of the artificial teeth in the gingival part.

FIG. 10a) shows an example where holes 1024 are modeled and manufactured in the gingival part 1003 to receive the manufactured teeth. In the FIG. 14 holes 1024 are provided, and thus this denture is configured for receiving 14 artificial teeth, which may be all the teeth of the lower or upper jaw of a patient. Thus this is a full denture for the upper or lower jaw. Fewer holes 1024 may be manufactured in the gingival part 1003, if the denture is not a full denture, but a partial denture.

Figure 10B:
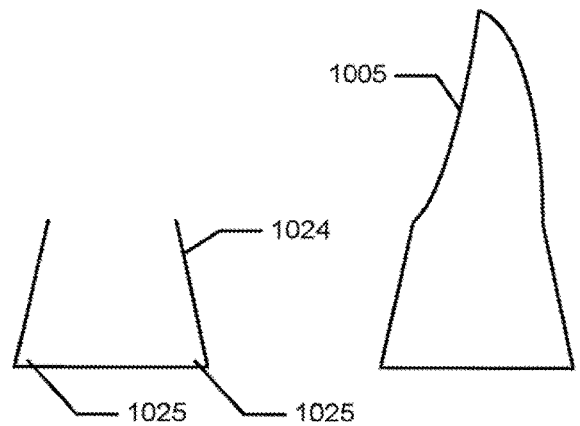

FIG. 10b) shows an example where the hole 1024 in the gingival part comprises undercuts 1025, whereby the artificial tooth 1006 can be attached in the hole 1024 by press-fitting.

Figure 10C:
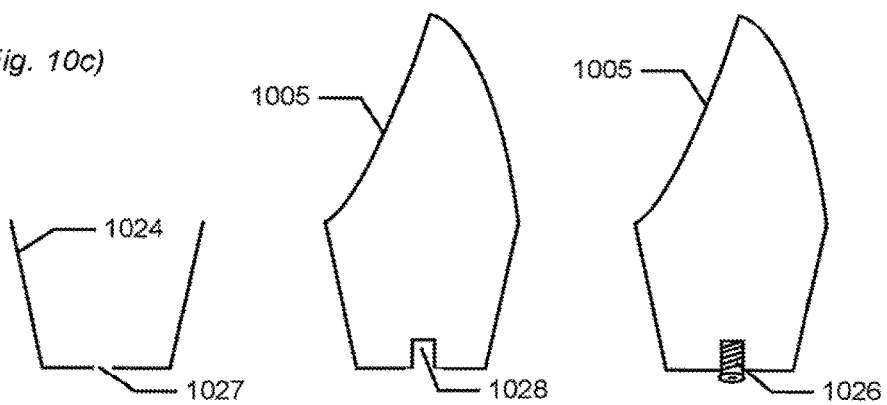

FIG. 10c) shows an example where the artificial tooth 1005 is attached in the hole 1024 of the gingival part by means of a fastening means in the form of a screw 1026 in the bottom of the hole 1024. A screw hole 1027 is manufactured in the bottom of the hole 1024, and a screw hole 1028 is manufactured in the bottom of the artificial tooth 1005.

Figure 10D:
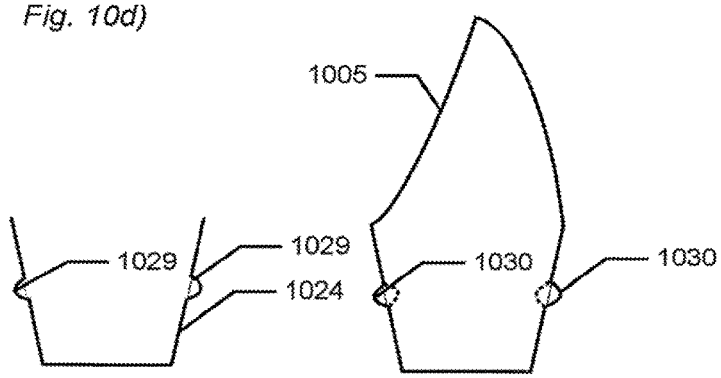

FIG. 10d) shows an example where the artificial tooth 1005 is attached in the hole 1024 in the gingival part by means of ball-shaped interlocking features 1029, 1030. The part of the interlocking feature in the hole 1024 may be denoted the hole interlocking feature 1029, and the part of the interlocking feature in the artificial tooth 1005 may be denoted the tooth interlocking feature 1030. The hole interlocking feature 1029 and the tooth interlocking feature 1030 match each other such that the tooth 1005 is fixed in the hole 1024 in the gingival part by means of the interlocking features 1029 and 1030.

There may be one or more, such as one, two, three, four or five sets of interlocking features for each artificial tooth.

The tooth interlocking feature 1030 may be configured to be pushed in to align with the plane surface of the tooth where it is arranged, for example when pressure is applied to the interlocking feature 1030, e.g. when a machine or a dental technician presses the interlocking feature 1030 in for pushing the artificial tooth 1005 in the hole 1024 in the gingival. When the artificial tooth 1005 has been pushed down into the hole 1024, the tooth interlocking feature 1030 is configured to push out again and file the space in the side wall of the hole 1024 provided by the corresponding hole interlocking feature 1029.

Figure 10E:
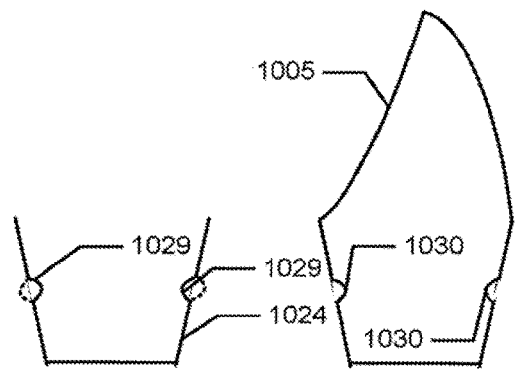

FIG. 10*e*) shows an example where the artificial tooth 1005 is attached in the hole 1024 in the gingival part by means of ball-shaped interlocking features 1029, 1030. The part of the interlocking feature in the hole 1024 may be denoted the hole interlocking feature 1029, and the part of the interlocking feature in the artificial tooth 1005 may be denoted the tooth interlocking feature 1030. The hole interlocking feature 1029 and the tooth interlocking feature 1030 match each other such that the tooth 1005 is fixed in the hole 1024 in the gingival part by means of the interlocking features 1029 and 1030.

There may be one or more, such as one, two, three, four or five sets of interlocking features for each artificial tooth.

The hole interlocking feature 1029 may be configured to be pushed in to align with the plane surface of the wall of the hole 1024 where it is arranged, for example when pressure is applied to the interlocking feature 1029, e.g. when a machine or a dental technician pushes the artificial tooth 1005 into the hole 1024 in the gingival. When the artificial tooth 1005 has been pushed down into the hole 1024, the hole interlocking feature 1029 is configured to push out again and file the space in the side wall of the tooth 1005 provided by the corresponding tooth interlocking feature 1030.

Figure 10F:
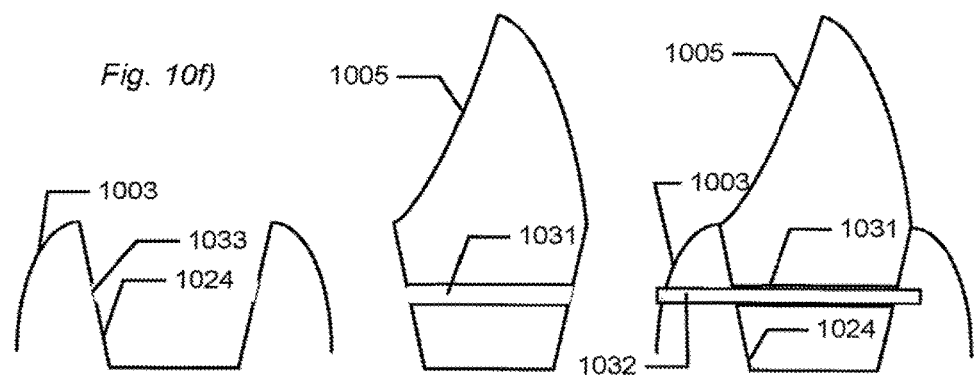

FIG. 10*f*) shows an example where the artificial tooth 1005 is attached in the gingival part by means of providing a bore 1031 in the area of the artificial teeth which is adapted to be arranged in the hole 1024 in the gingival part, and arranging a bar 1032 in the bore 1031, where the bar 1032 is adapted to extend outside the hole 1024 of the gingival part 1003 for retaining the artificial tooth 1005 in the gingival part 1003. The hole 1024 in the gingival part 1003 may comprises holes 1033 in the side walls of the hole 1024 such that the bar 1032 can fit in the hole 1024.

Alternatively and/or additionally the artificial teeth may be attached, e.g. in holes, in the gingival part by means of glue, cement, tape, vacuum or negative pressure created by means of moisture in the patient's mouth etc.

Figure 11:
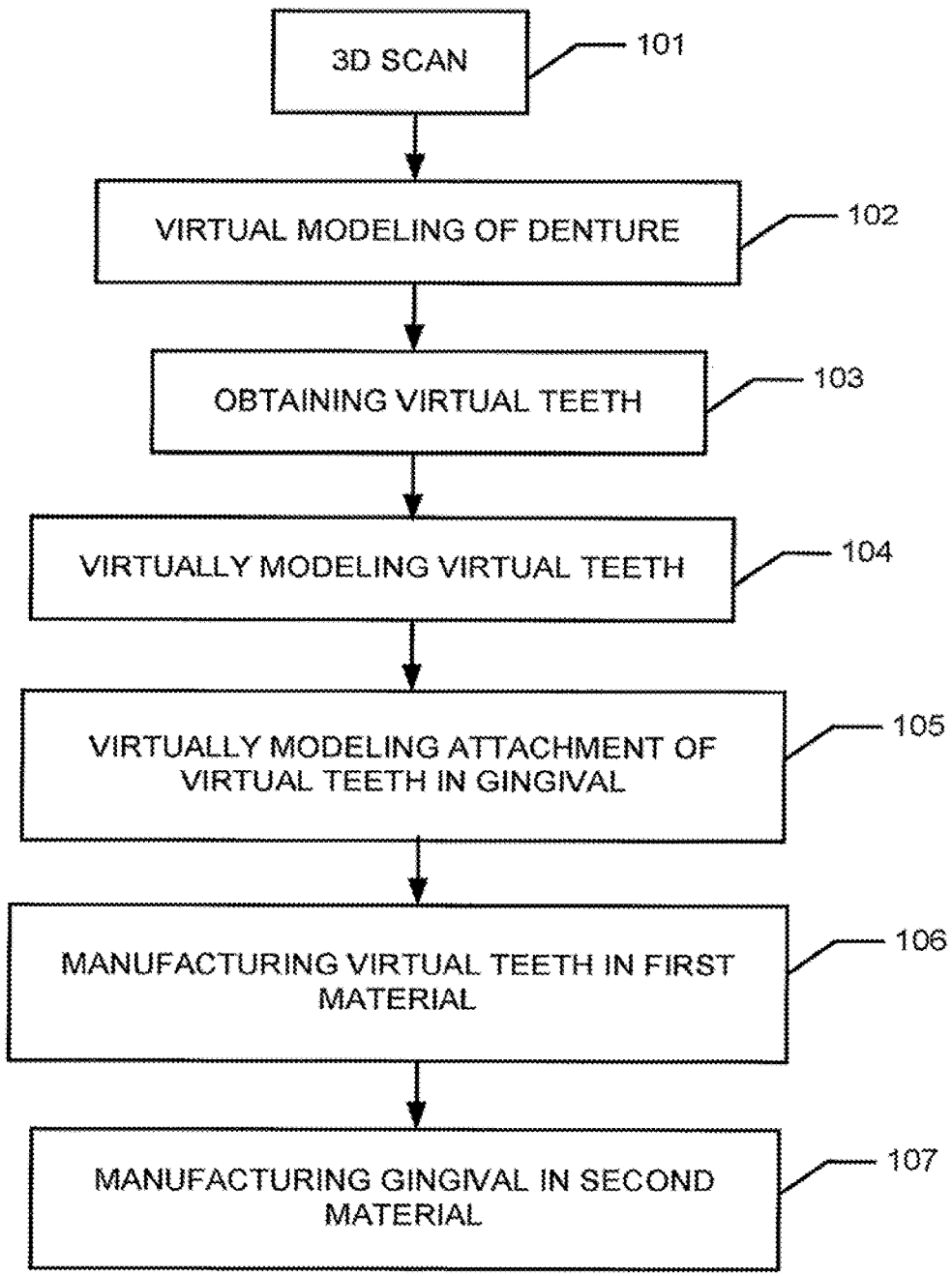
FIG. 11 shows an example of a flow chart of an aspect of the method.

FIG. 11 shows an example of a flow chart of the method for computer-aided modeling and computer-aided manufacturing of a denture comprising a gingival part and artificial teeth.

In step 101 a 3D scan comprising at least part of the patient's oral cavity os provided.

In step 102 at least part of the denture is virtually modeled using the 3D scan.

In step 103 virtual teeth is obtained to represent the artificial teeth.

In step 104 at least one of the virtual teeth is virtually modeled to obtain a set of modeled virtual teeth.

In step 105 attachment of the artificial teeth in the gingival part is virtually modeling for securing an fixing the artificial teeth in the gingival part.

In step 106 the modeled virtual teeth is manufactured in a first material.

In step 107 the gingival part is manufactured in a second material.

At least part of the denture is manufactured by means of computer aided manufacturing (CAM).

Although some embodiments have been described and shown in detail, the invention is not restricted to them, but may also be embodied in other ways within the scope of the subject matter defined in the following claims. In particular, it is to be understood that other embodiments may be utilised and structural and functional modifications may be made without departing from the scope of the present invention.

In device claims enumerating several means, several of these means can be embodied by one and the same item of hardware. The mere fact that certain measures are recited in mutually different dependent claims or described in different embodiments does not indicate that a combination of these measures cannot be used to advantage.

It should be emphasized that the term "comprises/comprising" when used in this specification is taken to specify the presence of stated features, integers, steps or components but does not preclude the presence or addition of one or more other features, integers, steps, components or groups thereof.

The features of the method described above and in the following may be implemented in software and carried out on a data processing system or other processing means caused by the execution of computer-executable instructions. The instructions may be program code means loaded in a memory, such as a RAM, from a storage medium or from another computer via a computer network. Alternatively, the described features may be implemented by hard-wired circuitry instead of software or in combination with software.

What is claimed is:

1. A method for creating a digital model of a denture for a patient, where the denture comprises a gingival part and artificial teeth, the method comprises:
    obtaining digital models of artificial teeth representing the artificial teeth;
    obtaining a 3D scan comprising a digital representation of at least part of the patient's existing gingiva;
    digitally modeling a gingival part of the digital model of the denture with the 3D scan and the digital artificial teeth;
    defining a first offset having a first thickness of a first portion of the gingival part of the digital model of the denture that extends from the digital representation of the at least part of the patient's existing gingiva; and
    defining a second offset having a second thickness of a second portion of the gingival part of the digital model of the denture that extends from the digital artificial teeth.

2. The method according to claim 1, wherein the method further comprises determining where an edge of the gingival part of the digital model of the denture ends with respect to the patient's existing gingiva.

3. The method according to claim 1, wherein the method further comprises determining where the gingival part of the digital model of the denture ends with respect to the digital artificial teeth.

4. The method according to claim 1, wherein the method further comprises determining a transition from the first portion of the gingival part to the second portion of the gingival part.

5. The method according to claim 4, wherein the transition is performed by a lofting operation.

6. The method according to claim 1, wherein the method further comprises modeling the gingival part based on a template gingiva.

7. The method according to claim 1, wherein the method further comprises modeling the gingival part based on a determined occlusal plane.

8. The method according to claim 1, wherein the method further comprises using offsetting, lofting and/or smooth transitioning to model the gingival part relative to the existing gingiva and the digital models of artificial teeth.

9. The method according to claim 1, wherein the method further comprises applying a stipple wax pattern on the gingival part of the digital model of the denture.

10. The method according to claim 1, wherein the method further comprises smoothing a nonvisible part of the gingival part of the digital model of the denture to aid with cleaning.

11. The method according to claim 1, wherein the method further comprises arranging a position of the digital models of artificial teeth in the gingival part of the digital model of the denture based on predetermined rules or criteria.

12. The method according to claim 1, wherein the digital models of the artificial teeth represent a composed set of teeth comprising a number of teeth arranged spatially relative to each other.

13. The method according to claim 1, wherein the denture is configured to attach to dental implants and/or on dental implant bars or bridges.

14. The method according to claim 1, wherein the method further comprises modeling the denture and dental implants and/or a dental implant bar or a bridge to fit each other.

15. The method according to claim 1, wherein the method further comprises arranging the digital models of artificial teeth spatially relative to each other.

16. A method for creating a digital model of a denture for a patient, where the denture comprises a gingival part and artificial teeth, and manufacturing a denture for a patient, the method comprises:
  obtaining digital models of artificial teeth representing the artificial teeth;
  obtaining a 3D scan comprising a digital representation of at least part of the patient's existing gingiva;
  digitally modeling a gingival part of the digital model of the denture with the 3D scan and the digital artificial teeth;
  defining a first offset having a first thickness of a first portion of the gingival part of the digital model of the denture that extends from the digital representation of the at least part of the patient's existing gingiva;
  defining a second offset having a second thickness of a second portion of the gingival part of the digital model of the denture that extends from the digital artificial teeth;
  manufacturing the digital models of artificial teeth in a first material;
  manufacturing the gingival part in a second material; and
  manufacturing at least part of the denture by means of computer aided manufacturing (CAM).

17. The method according to claim 16, wherein the method further comprises that at least the gingival part of the denture is manufactured by means of 3D printing.

18. The method according to claim 16, wherein the method further comprises that at least the gingival part is manufactured by means of milling.

19. The method according to claim 16, wherein the method further comprises modeling and manufacturing holes in the gingival part to receive the manufactured teeth.

20. The method according to claim 16, wherein the method further comprises determining where an edge of the gingival part of the digital model of the denture ends with respect to the patient's existing gingiva.

21. The method according to claim 16, wherein the method further comprises determining where the gingival part of the digital model of the denture ends with respect to the digital artificial teeth.

22. The method according to claim 16, wherein the method further comprises determining a transition from the first portion of the gingival part to the second portion of the gingival part.

23. The method according to claim 16, wherein the method further comprises arranging the digital models of artificial teeth spatially relative to each other.

* * * * *